United States Patent
Sage et al.

(10) Patent No.: US 9,068,587 B2
(45) Date of Patent: Jun. 30, 2015

(54) SET SCREW APPARATUS

(71) Applicant: Greatbatch Ltd., Clarence, NY (US)

(72) Inventors: Shahn S. Sage, Andover, MN (US); Tom Walch, Centerville, MN (US); Andrew Richardson, Chanhassen, MN (US); Erik Jagger, Deephaven, MN (US)

(73) Assignee: Greatbach Ltd., Clarence, NY (US)

( * ) Notice: Subject to any disclaimer, the term of this patent is extended or adjusted under 35 U.S.C. 154(b) by 105 days.

(21) Appl. No.: 14/032,316

(22) Filed: Sep. 20, 2013

(65) Prior Publication Data

US 2015/0086292 A1   Mar. 26, 2015

(51) Int. Cl.
*F16B 35/00* (2006.01)
*F16B 39/22* (2006.01)
*F16B 41/00* (2006.01)

(52) U.S. Cl.
CPC ............... *F16B 39/22* (2013.01); *F16B 35/005* (2013.01); *F16B 41/002* (2013.01)

(58) Field of Classification Search
CPC ..... F16B 35/04; F16B 41/002; F16B 23/0092
USPC .......................................... 411/393, 999, 410
See application file for complete search history.

(56) References Cited

U.S. PATENT DOCUMENTS

| | | | | |
|---|---|---|---|---|
| 278,759 A * | 6/1883 | Wallensak | | 411/393 |
| 1,187,430 A * | 6/1916 | Kenly | | 24/275 |
| 1,487,682 A * | 3/1924 | Leppert | | 439/737 |
| 2,295,314 A * | 9/1942 | Whitney | | 411/393 |
| 3,260,989 A * | 7/1966 | Curtis | | 439/812 |
| 3,346,835 A | 10/1967 | Burniston | | |
| 3,424,212 A * | 1/1969 | Kemper | | 81/436 |
| 3,426,321 A * | 2/1969 | Peterson, Jr. | | 439/742 |
| 3,434,103 A * | 3/1969 | Hancock et al. | | 439/812 |
| 3,737,839 A | 6/1973 | Marechal | | |
| 4,027,940 A | 6/1977 | Mazzeo | | |
| 4,304,424 A * | 12/1981 | Hansen | | 285/111 |
| 4,316,471 A | 2/1982 | Shipko et al. | | |
| 5,052,643 A * | 10/1991 | Law | | 248/56 |
| 5,580,286 A | 12/1996 | Kramer et al. | | |
| 5,713,705 A * | 2/1998 | Grunbichler | | 411/5 |
| 7,210,968 B1 | 5/2007 | Gister et al. | | |
| 7,308,312 B1 | 12/2007 | Lim et al. | | |
| 7,402,076 B1 | 7/2008 | Lim et al. | | |
| 8,032,221 B2 | 10/2011 | Wengreen et al. | | |
| 8,241,074 B2 | 8/2012 | Watford et al. | | |

FOREIGN PATENT DOCUMENTS

DE   19513281   10/1996

\* cited by examiner

*Primary Examiner* — Flemming Saether
(74) *Attorney, Agent, or Firm* — Michael P. Horvath

(57) ABSTRACT

In various examples, a set screw apparatus includes a set screw including a set screw body. An abutment extends radially outwardly from the set screw body and longitudinally separated from a threaded set screw area of a first length by an unthreaded set screw area of a second length of the set screw body. A block includes a bore. A threaded block area includes a third length, wherein the abutment inhibits movement of the set screw past the threaded block area and removal of the set screw from the bore. The third length is shorter than the second length so that an entirety of the threaded block area can be disposed within the unthreaded set screw area, such that the set screw is freely rotatable within the bore, but retained within the bore, if turned in a first direction with respect to the block.

18 Claims, 4 Drawing Sheets

SET SCREW APPARATUS

BACKGROUND

The present invention relates to a set screw apparatus, and more specifically relates to a set screw apparatus for retaining a therapy delivery element with respect to a device.

Implantable medical devices often include headers having set screw and block assemblies for retaining leads and other such devices in connection with the implantable medical devices. However, if the set screw is completely backed out of the block, the set screw will disengage from and potentially fall out of the block. The set screw can often be very difficult, if not impossible, to re-engage within the block. If the set screw is able to be re-engaged within the blocks, doing so costs valuable time and effort. If the set screw is unable to be re-engaged, the implantable medical device might have to be replaced, which, in addition to costing time and effort, can cost a considerable amount of money. Moreover, if the set screw falls out of the block and into the patient, time and effort must be spent to locate the set screw and remove the set screw from within the patient. There also exists a possibility of potential health issues arising from the set screw falling into the patient.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that set screw apparatuses can be configured to retain a set screw within a block even when threads of the set screw are completely backed out from threads of the block. In this way, the possibility of the set screw falling out of the block is reduced, if not eliminated, thereby reducing, if not eliminating, additional costs, time, effort, or health complications associated with the set screw falling out of the block and/or the re-engagement of the set screw with the block or the replacement of the device with which the set screw apparatus is associated. To better illustrate the apparatuses and methods described herein, a non-limiting list of examples is provided here:

Example 1 can include subject matter that can include a set screw apparatus including a set screw and a block. The set screw includes a set screw body. One or more set screw threads extend radially outwardly from the set screw body and are disposed along a threaded set screw area of the set screw body. The threaded set screw area includes a first length measured longitudinally along the set screw body. An abutment extends radially outwardly from the set screw body and is longitudinally separated from the threaded set screw area by an unthreaded set screw area of the set screw body. The unthreaded set screw area includes a second length measured longitudinally along the set screw body. The block includes a bore sized and shaped to accept the set screw within the bore. One or more block threads extend radially inwardly from the bore and are disposed along a threaded block area of the bore. The one or more block threads are complementary with the one or more set screw threads so as to be threadably engageable with the one or more set screw threads. The threaded block area includes a third length measured longitudinally along the bore, wherein the abutment is sized and shaped to abut, but not threadably engage with, the one or more block threads to inhibit movement of the set screw past the threaded block area and removal of the set screw from the bore. The third length is shorter than the second length so that an entirety of the threaded block area can be disposed within the unthreaded set screw area between the threaded set screw area and the abutment, such that, with the threaded block area disposed within the unthreaded set screw area the set screw is freely rotatable within the bore, but retained within the bore, if turned in a first direction with respect to the block, and the one or more set screw threads are threadably engageable with the one or more block threads to move the set screw in an inward direction with respect to the block with the set screw turned in a second direction with respect to the block.

In Example 2, the subject matter of Example 1 is optionally configured such that the abutment is integrally formed with the set screw body.

In Example 3, the subject matter of any one of Examples 1-2 is optionally configured such that the set screw body includes a cylindrical shape.

In Example 4, the subject matter of any one of Examples 1-3 is optionally configured such that the set screw body is substantially tubular.

In Example 5, the subject matter of any one of Examples 1-4 is optionally configured such that the abutment is disposed proximate a distal end of the set screw body.

In Example 6, the subject matter of any one of Examples 1-5 is optionally configured such that the abutment is substantially annular.

In Example 7, the subject matter of any one of Examples 1-6 is optionally configured such that the threaded set screw area is disposed at a proximal end of the set screw body.

In Example 8, the subject matter of any one of Examples 1-7 is optionally configured such that the block includes a passage fluidly coupled with the bore. The passage is configured to selectively accept a proximal end of a therapy delivery element, wherein, with the proximal end of the therapy delivery element disposed within the passage, rotation of the set screw in the second direction with respect to the block causes the set screw to move in the inward direction with respect to the block to bear against the proximal end of the therapy delivery element.

In Example 9, the subject matter of Example 8 is optionally configured such that the passage is oriented within the block substantially perpendicularly to the bore.

In Example 10, the subject matter of any one of Examples 1-9 is optionally configured such that the set screw includes a tool engagement opening configured to accept at least a portion of a tool within the tool engagement opening to facilitate rotation of the set screw with respect to the block.

In Example 11, the subject matter of Example 10 is optionally configured such that the tool engagement opening is configured to allow engagement of at least the portion of the tool with the tool engagement opening from a proximal end of the set screw body and from a distal end of the set screw body.

In Example 12, the subject matter of Example 10 is optionally configured such that the tool engagement opening extends entirely through the set screw body to allow engagement of at least the portion of the tool with the tool engagement opening from the proximal end of the set screw body and from the distal end of the set screw body.

Example 13 can include, or can optionally be combined with any one of Examples 1-12 to include subject matter that can include a set screw apparatus including a set screw and a block. The set screw includes a set screw body including a proximal end and a distal end. One or more set screw threads extend radially outwardly from the set screw body and are disposed along a threaded set screw area of the set screw body. The threaded set screw area includes a first length measured longitudinally along the set screw body. The threaded set screw area is disposed at the proximal end of the set screw body. An abutment extends radially outwardly from and is integrally formed with the set screw body and is longitudinally separated from the threaded set screw area by an unthreaded set screw area of the set screw body. The unthreaded set screw area includes a second length measured longitudinally along the set screw body. The abutment is disposed proximate the distal end of the set screw body. A tool engagement opening is disposed within the set screw body. The tool engagement opening is configured to accept at least a portion of a tool within the tool engagement opening. The tool engagement opening extends entirely through the set screw body to allow engagement of at least the portion of the tool with the tool engagement opening from the proximal end of the set screw body and from the distal end of the set screw body. The block includes a bore sized and shaped to accept the set screw within the bore. One or more block threads extend radially inwardly from the bore and are disposed along a threaded block area of the bore. The one or more block threads are complementary with the one or more set screw threads so as to be threadably engageable with the one or more set screw threads. The threaded block area includes a third length measured longitudinally along the bore, wherein the abutment is sized and shaped to abut, but not threadably engage with, the one or more block threads to inhibit movement of the set screw past the threaded block area and removal of the set screw from the bore. The third length is shorter than the second length so that an entirety of the threaded block area can be disposed within the unthreaded set screw area between the threaded set screw area and the abutment, such that, with the threaded block area disposed within the unthreaded set screw area the set screw is freely rotatable within the bore, but retained within the bore, if turned in a first direction with respect to the block, and the one or more set screw threads are threadably engageable with the one or more block threads to move the set screw in an inward direction with respect to the block with the set screw turned in a second direction with respect to the block.

In Example 14, the subject matter of Example 13 is optionally configured such that the set screw body includes a cylindrical shape.

In Example 15, the subject matter of any one of Examples 13-14 is optionally configured such that the set screw body is substantially tubular.

In Example 16, the subject matter of any one of Examples 13-15 is optionally configured such that the abutment is substantially annular.

In Example 17, the subject matter of any one of Examples 13-16 is optionally configured such that the block includes a passage fluidly coupled with the bore. The passage is configured to selectively accept a proximal end of a therapy delivery element, wherein, with the proximal end of the therapy delivery element disposed within the passage, rotation of the set screw in the second direction with respect to the block causes the set screw to move in the inward direction with respect to the block to bear against the proximal end of the therapy delivery element.

In Example 18, the subject matter of Example 17 is optionally configured such that the passage is oriented within the block substantially perpendicularly to the bore.

DETAILED DESCRIPTION

Figure 1:
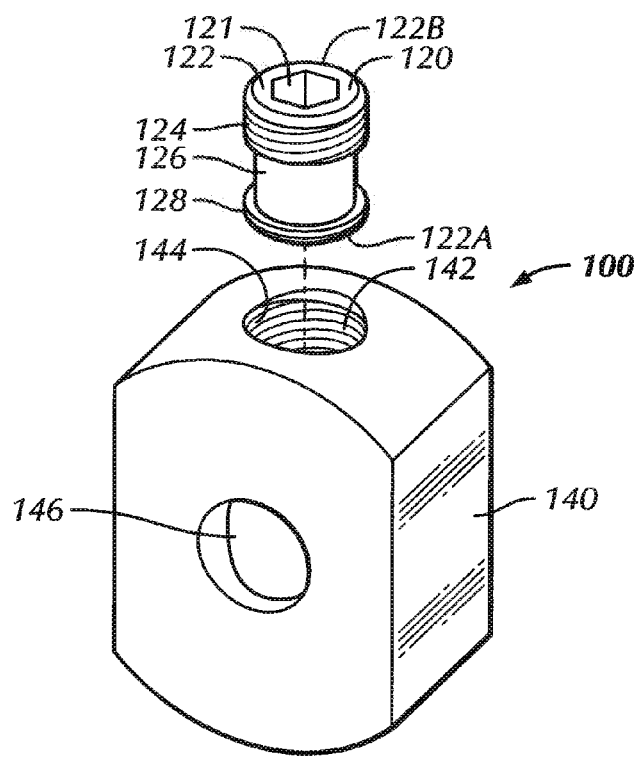
FIG. 1 is an exploded perspective view of a set screw apparatus in accordance with at least one example of the invention.
Figure 2:
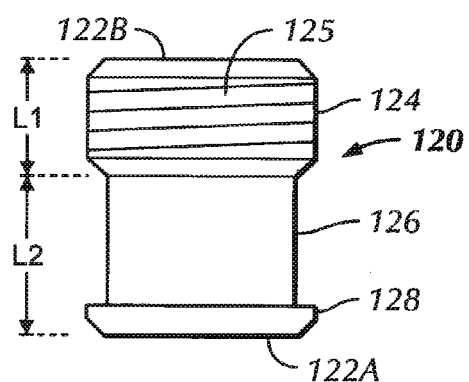
FIG. 2 is a side view of a set screw in accordance with at least one example of the invention.
Figure 3:
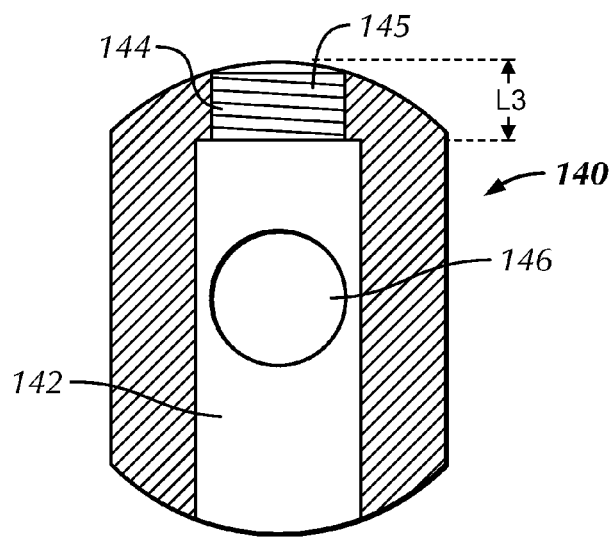
FIG. 3 is a cross-sectional view of a block in accordance with at least one example of the invention.
Figure 4:
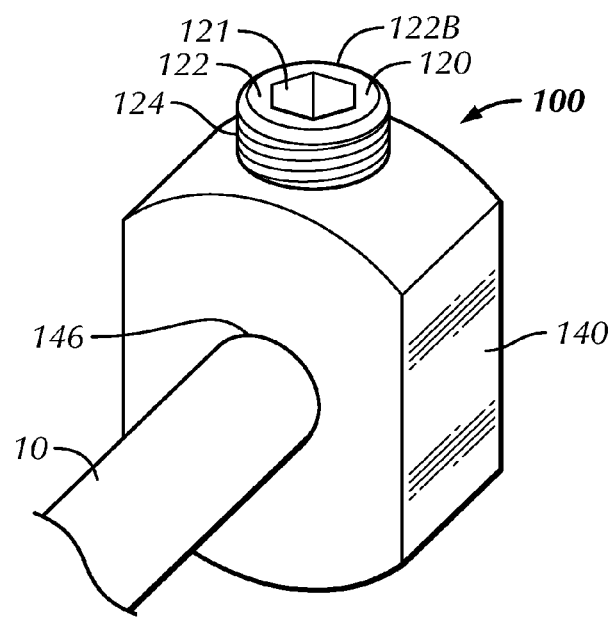
FIG. 4 is a perspective view of a set screw apparatus in accordance with at least one example of the invention.

The present patent application relates to a set screw apparatus. In various examples, as described herein, the set screw apparatus is configured to retain a therapy delivery element (or an extension for a therapy delivery element) with respect to a device. In various examples, as described herein, the set screw apparatus includes a set screw that will be retained within a block even if the set screw is backed out completely from the block. In this way, the examples of set screw apparatuses described herein can reduce, if not eliminate, expenditures of time, effort, and/or money due to set screws being completely backed out of and disengaged from the blocks (accidentally or otherwise).

Although the examples of set screw apparatuses are mostly described herein with respect to retention of a therapy delivery element (or an extension for a therapy delivery element) within a medical device, it should be noted that this is for the sake of convenience and should not be limited as such. The present subject matter can be applied to retention of devices other than therapy delivery elements with respect to medical devices. Moreover, the present subject matter can be applied to areas other than the medical device area. For instance, the present subject matter can be applied to any set screw configuration.

Referring to FIGS. 1-4, in some examples, a set screw apparatus 100 is configured to retain a device, such as, but not limited to, a therapy delivery element 10 (or an extension for a therapy delivery element), on, in, or otherwise with respect to another device, such as, but not limited to, a pulse generator. In some examples, the set screw apparatus 100 is configured to be implemented in a header or other such assembly of a medical device, the header or other such assembly being configured to accept and/or retain one or more therapy delivery elements 10 (or extensions). In some examples, the set screw apparatus 100 includes a set screw 120 and a block 140 configured to accept the set screw 120.

In some examples, the set screw 120 includes a set screw body 122. In some examples, the set screw body 122 includes a cylindrical shape. The set screw body 122, in some examples, includes a distal end 122A and a proximal end 122B. In some examples, the proximal end 122B of the set screw body 122 includes a tool engagement opening 121. Although shown as a hexagonal opening in the figures, it is contemplated that the tool engagement opening 121 include any shape to accommodate a tool for rotating the set screw 120 with respect to the block 140, such as, but not limited to a hex wrench, a slot head screw driver, a Phillips head screw driver, a hexalobular wrench, or the like.

In some examples, the tool engagement opening 121 extends a distance into the set screw body 122. In further examples, the tool engagement opening 121 extends entirely through the set screw body 122 from the proximal end 122B to the distal end 122A. In some examples, the set screw body 122 is substantially tubular. In some examples, with the tool engagement opening 121 extending entirely through the set screw body 122, it allows access to the tool engagement opening 121 from both the distal end 122A and the proximal end 122B of the set screw 120. Providing access to the tool engagement opening 121 from the distal end 122A facilitates initial insertion and threading of the set screw 120 into the block 140 to assemble the set screw apparatus 100, which, in some examples, is accomplished by inserting the set screw into the bore 142 from a bottom of the block 140 and rotating the set screw 120 with respect to the block 140 using a corresponding tool within the tool engagement opening 121 at the distal end 122A of the set screw 120. In some examples, the tool engagement opening 121 extending entirely through the set screw body 122 allows for a larger amount of surface area against which a corresponding tool interacts to rotate the set screw 120 with respect to the block 140 than if the tool engagement opening extended only partially through the set screw. The larger amount of surface area, in some examples, can reduce the possibility of stripping or otherwise damaging the tool engagement opening 121 of the set screw 122 by distributing forces encountered during rotation of the set screw 120 using a corresponding tool over a larger area. In some examples, the set screw can include separate tool engagement openings at each of the distal end and the proximal end, such that the tool engagement openings are not fluidly coupled with one another. That is, one tool engagement opening extends from the proximal end of the set screw a distance into the set screw, and the other tool engagement opening extends from the distal end of the set screw a distance into the set screw without intersecting the tool engagement opening of the proximal end. Such an arrangement would allow for rotation of the set screw from both the proximal end and the distal end using a corresponding tool, while, at the same time, not providing an open pathway through the set screw between the distal end and the proximal end. It should be understood that, in various examples, the tool engagement opening 121 can be configured in various ways, provided that the tool engagement opening 121 allows a user to rotate the set screw 120 with respect to the block 140 using a corresponding tool, for instance, to tighten the set screw 120 against a portion of a therapy delivery element 10 (or extension) in order to retain the therapy delivery element 10 (or extension) with a medical device or to loosen the set screw 120, for instance, to remove the therapy delivery element 10 (or extension) from the medical device.

In some examples, the set screw 120 includes one or more set screw threads 125 extending radially outwardly from the set screw body 122 and disposed along a threaded set screw area 124 of the set screw body 122. The threaded set screw area 124, in some examples, includes a first length L1 (FIG. 2) measured longitudinally along the set screw body 122. In some examples, the threaded set screw area 124 is disposed at the proximal end 122B of the set screw body 122. In other examples, the threaded set screw area can be disposed at any point along the set screw body 122.

In some examples, the set screw 120 includes an abutment 128 extending radially outwardly from the set screw body 122 and longitudinally separated from the threaded set screw area 124 by an unthreaded set screw area 126 of the set screw body 122. In some examples, the unthreaded set screw area 126 includes a second length L2 (FIG. 2) measured longitudinally along the set screw body 122. In some examples, the abutment 128 is integrally formed with the set screw body 122. In some examples, the abutment 128 is disposed proximate the distal end 122A of the set screw body 122. The abutment 128, in some examples, is substantially annular. In some examples, the abutment 128 extends from the set screw body 122 completely around the set screw body 122. In some examples, the abutment extends partially around the set screw body. In some examples, the abutment is segmented around or partially around the set screw body.

Figure 5:
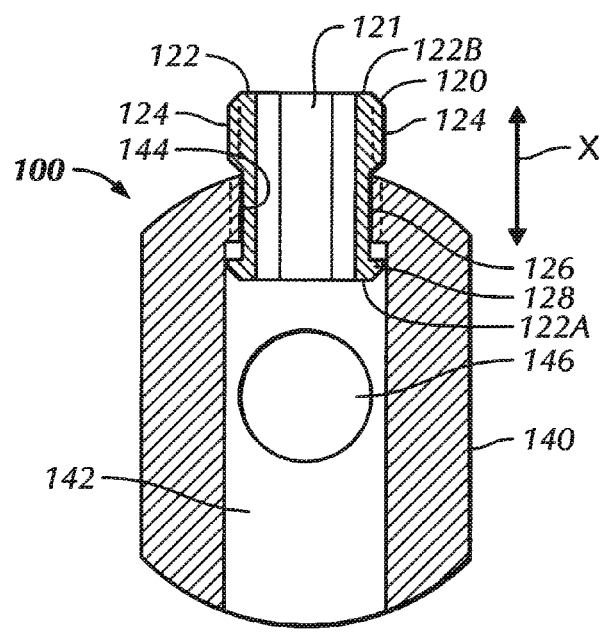
FIG. 5 is a cross-sectional view of a set screw apparatus in accordance with at least one example of the invention.
Figure 6:
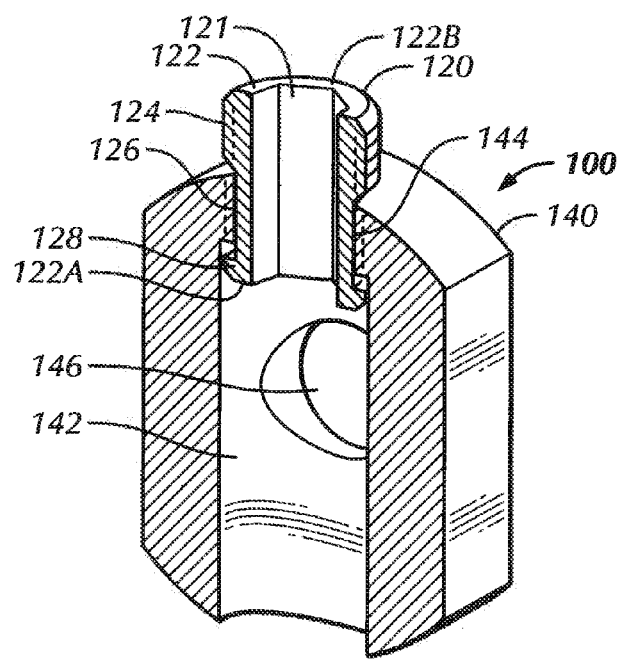
FIG. 6 is a cross-sectional perspective view of a set screw apparatus in accordance with at least one example of the invention.

Referring now to FIGS. 1-6, in some examples, the block 140 includes a bore 142 sized and shaped to accept the set screw 120 within the bore 142. In some examples, the block 140 includes one or more block threads 145 extending radially inwardly from the bore 142 and disposed along a threaded block area 144 of the bore 142. The one or more block threads 145, in some examples, are complementary with the one or more set screw threads 125 so as to be threadably engageable with the one or more set screw threads 125, such that rotation of the set screw 120 with respect to the block 140 causes the set screw 120 to move longitudinally within the bore 142 along arrow X (FIG. 5).

Figure 7:
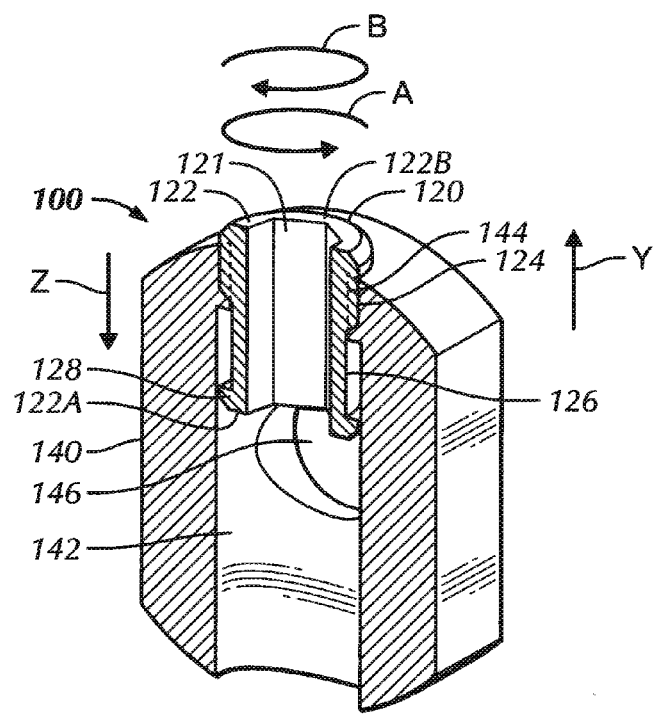
FIG. 7 is a cross-sectional perspective view of a set screw apparatus in accordance with at least one example of the invention and showing motion of a set screw threadably engaged with a block.
Figure 8:
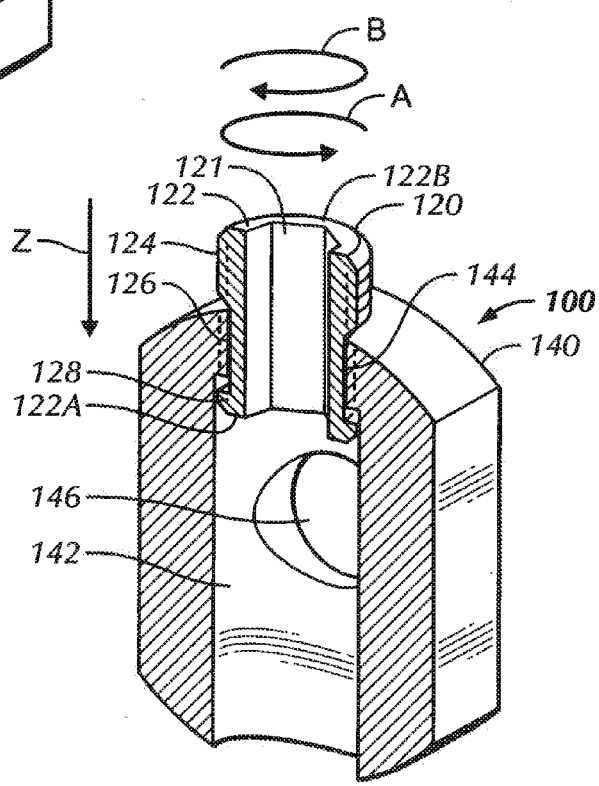
FIG. 8 is a cross-sectional perspective view of a set screw apparatus in accordance with at least one example of the invention and showing motion of a set screw not threadably engaged with a block.

Referring briefly to FIGS. 7 and 8, in some examples, rotation of the set screw 120 with respect to the block 140 in a first direction A causes the set screw 120 to move longitudinally within the bore 142 along arrow Y. In some examples, rotation of the set screw 120 with respect to the block 140 in a second direction B causes the set screw 120 to move longitudinally within the bore 142 along arrow Z. In some examples, the first direction A is opposite the second direction B. In some examples, the direction A is counterclockwise, and the direction B is clockwise. In this way, rotation of the set screw 120 moves the set screw 120 outwardly (along the arrow Y) or inwardly (along the arrow Z) with respect to the bore 142, for instance, to release or retain, respectively, a portion of a therapy delivery element 10 (FIG. 4) (or extension) within the block 140 using the set screw 120.

Referring again to FIGS. 1-6, in some examples, the threaded block area 144 includes a third length L3 (FIG. 3) measured longitudinally along the bore 142. In some examples, the abutment 128 is sized and shaped to abut, but not threadably engage with, the one or more block threads 145. In this way, this configuration inhibits movement of the set screw 120 past the threaded block area 144 and removal of the set screw 120 from the bore 142.

Referring to FIGS. 2, 3, 7, and 8, in some examples, the third length L3 is shorter than the second length L2 so that an entirety of the threaded block area 144 can be disposed within the unthreaded set screw area 126 between the threaded set screw area 124 and the abutment 128. In this way, with the threaded block area 144 disposed within the unthreaded set screw area 126, as is seen in FIG. 8, the set screw 120 is freely rotatable within the bore 142, but retained within the bore 142, if turned in the first direction A with respect to the block 140. That is, once the threaded block area 144 is disposed within the unthreaded set screw area 126, rotation of the set screw 120 in the first direction A ceases to produce movement in the outward direction Y of the set screw 120 with respect to the bore 142 because the one or more set screw threads 125 are no longer threadably engaged with the one or more block threads 145 and/or because the abutment 128 is inhibiting the set screw 120 from moving farther in the outward direction Y with respect to the bore 142. However, the one or more set screw threads 125 are threadably engageable with the one or more block threads 145 to move the set screw 120 in the inward direction Z with respect to the block 140 with the set screw 120 turned in the second direction B with respect to the block 140.

Referring to FIGS. 4-8, in some examples, the block 140 includes a passage 146 fluidly coupled with the bore 142. In some examples, the passage 146 is oriented within the block 140 substantially perpendicularly to the bore 142. In some examples, the passage 146 is configured to selectively accept a proximal end of a therapy delivery element 10 (or extension). With the proximal end of the therapy delivery element 10 (or extension) disposed within the passage 146, in some examples, rotation of the set screw 120 in the second direction B with respect to the block 140 causes the set screw 120 to move in the inward direction Z with respect to the block 140 to bear against the proximal end of the therapy delivery element 10. In some examples, one or more passages 146 of one or more blocks 140 can be disposed within a header (for instance, of a medical device), the number of blocks 140 and passages 146 corresponding to a number of therapy delivery elements 10 (or extensions) that are to be attached to the header. In some examples, the set screw apparatus 100 can be used with an implantable medical device.

In this way, in some examples, the set screw 120 can be used to retain the proximal end of the therapy delivery element 10 (or extension) within the block 140. For instance, in some examples, prior to inserting the proximal end of the therapy delivery element 10 (or extension) into the passage 146 (or in order to remove an already-inserted proximal end of the therapy delivery element 10 or extension from the passage 146), the set screw 120 can be rotated in the first direction A to move the set screw 120 in the outward direction Y with respect to the bore 142 and the passage 146 and leave the passage 146 unobstructed by the set screw 120 (FIG. 5). Because of the configuration of the set screw 120 of the present subject matter, in some examples, a physician or other user rotating the set screw 120 need not worry about the set screw 120 releasing, dislodging, or otherwise falling out of the block 140 if the physician or other user rotates the set screw 120 more than is necessary in the first direction A. In some examples, instead of releasing, dislodging, or otherwise falling out of the block 140, with the threaded block area 144 disposed within the unthreaded set screw area 126, the set screw 120 will become captive in the block 140 and freely rotate with respect to the block 140 when rotated in the first direction A. In some examples, the abutment 128 inhibits the set screw 120 from being removed from within the bore 140, for instance, if an outward force is applied to the set screw. In various examples, such an outward force applied to the set screw 120 could result from gravity if the set screw apparatus 100 is held with the set screw 120 facing in a substantially downward direction, from higher pressure within the block 140 than outside the block 140, from a pulling force applied to the set screw 120, or the like. With the passage 146 unobstructed by the set screw 120, the proximal end of the therapy delivery element 10 (or extension) can be inserted within (or removed from) the passage 146. If inserting the proximal end of the therapy delivery element 10 (or extension), once inserted, the physician or other user can rotate the set screw 120 in the second direction B to move the set screw 120 in the inward direction Z to allow the set screw 120 to contact and bear against the proximal end of the therapy delivery element 10 (or extension), thereby positively engaging the proximal end of the therapy delivery element 10 (or extension) with the set screw apparatus 100 and retaining or helping to retain the proximal end of the therapy delivery element 10 (or extension) within the header or other device with which the set screw apparatus 100 is being used.

The present inventors have recognized various advantages of the subject matter described herein. For instance, in some examples, the set screw apparatus retains the set screw within the block even when the threads of the set screw are completely backed out from the threads of the block. In this way, the possibility of the set screw falling out of the block is reduced, if not eliminated, thereby reducing, if not eliminating, additional costs, time, effort, or health complications associated with the set screw falling out of the block and/or the re-engagement of the set screw with the block or the replacement of the device with which the set screw apparatus is associated. While various advantages of the example apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A set screw apparatus comprising:
   a set screw including:
     a set screw body including a first screw end and a second screw end;
     one or more set screw threads extending radially outwardly from the set screw body and disposed along a threaded set screw area of the set screw body, the threaded set screw area extending from the first screw end toward the second screw end and including a first length measured longitudinally along the set screw body; and
     an abutment extending radially outwardly from the set screw body proximate the second screw end and longitudinally separated from the threaded set screw area by an unthreaded set screw area of the set screw body, the unthreaded set screw area including a second length measured longitudinally along the set screw body; and
   a block including:
     a bore sized and shaped to accept the set screw within the bore for threadably engaging the set screw within the bore, the first screw end being configured to fit within and pass through an opening of the bore in order to insert the set screw into the bore; and
     one or more block threads extending radially inwardly from the bore and disposed along a threaded block area of the bore, the one or more block threads being complementary with the one or more set screw threads so as to be threadably engageable with the one or more set screw threads, the threaded block area including a third length measured longitudinally along the bore, wherein the abutment of the set screw is sized and shaped to abut, but not threadably engage with, the one or more block threads to inhibit movement of the set screw and outwardly past the threaded block area away from the opening of the bore to thereby inhibit removal of the set screw from the bore, the third length being shorter than the second length so that an entirety of the threaded block area can be disposed within the unthreaded set screw area between the threaded set screw area and the abutment, such that, with the threaded block area disposed within the unthreaded set screw area:
       if turned in a first direction with respect to the block, the set screw is freely rotatable within the bore, but retained within the bore as the abutment of the set screw abuts the one or more block threads; and
       if turned in a second direction, opposite the first direction, with respect to the block, the one or more set screw threads are threadably engageable with the one or more block threads to move the set screw in an inward direction toward the opening of the bore.

2. The set screw apparatus of claim 1, wherein the abutment is integrally formed with the set screw body.

3. The set screw apparatus of claim 1, wherein the set screw body includes a cylindrical shape.

4. The set screw apparatus of claim 1, wherein the set screw body is substantially tubular.

5. The set screw apparatus of claim 1, wherein the abutment is disposed proximate a distal end of the set screw body.

6. The set screw apparatus of claim 1, wherein the abutment is substantially annular.

7. The set screw apparatus of claim 1, wherein the threaded set screw area is disposed at a proximal end of the set screw body.

8. The set screw apparatus of claim 1, wherein the block includes a passage fluidly coupled with the opening of the bore, the passage configured to selectively accept a proximal end of a therapy delivery element, wherein, with the proximal end of the therapy delivery element disposed within the passage, rotation of the set screw in the second direction with respect to the block causes the set screw to move in the inward direction with respect to the block to bear against the proximal end of the therapy delivery element.

9. The set screw apparatus of claim 8, wherein the passage is oriented within the block substantially perpendicularly to the bore.

10. The set screw apparatus of claim 1, wherein the set screw includes a tool engagement opening configured to accept at least a portion of a tool within the tool engagement opening to facilitate rotation of the set screw with respect to the block.

11. The set screw apparatus of claim 10, wherein the tool engagement opening is configured to allow engagement of at least the portion of the tool with the tool engagement opening from a proximal end of the set screw body and from a distal end of the set screw body.

12. The set screw apparatus of claim 10, wherein the tool engagement opening extends entirely through the set screw body to allow engagement of at least the portion of the tool with the tool engagement opening from the proximal end of the set screw body and from the distal end of the set screw body.

13. A set screw apparatus comprising:
   a set screw including:
     a set screw body including a proximal screw end and a distal screw end;
     one or more set screw threads extending radially outwardly from the set screw body and disposed along a threaded set screw area of the set screw body, the threaded set screw area including a first length measured longitudinally along the set screw body, the threaded set screw area extending from the proximal screw end toward the distal screw end;
     an abutment extending radially outwardly from and integrally formed with the set screw body and longitudinally separated from the threaded set screw area by an unthreaded set screw area of the set screw body, the unthreaded set screw area including a second length measured longitudinally along the set screw body, the abutment disposed proximate the distal screw end; and
     a tool engagement opening within the set screw body, the tool engagement opening configured to accept at least a portion of a tool within the tool engagement opening, the tool engagement opening extending entirely through the set screw body to allow engagement of at least the portion of the tool with the tool engagement opening from the proximal end of the set screw body and from the distal end of the set screw body; and
   a block including:
     a bore sized and shaped to accept the set screw within the bore for threadably engaging the set screw within the bore, the proximal end of the set screw being configured to fit within and pass through an opening of the bore in order to insert the set screw into the bore; and
     one or more block threads extending radially inwardly from the bore and disposed along a threaded block area of the bore, the one or more block threads being complementary with the one or more set screw threads so as to be threadably engageable with the one or more set screw threads, the threaded block area including a third length measured longitudinally along the bore, wherein the abutment of the set screw is sized and shaped to abut, but not threadably engage with, the one or more block threads to inhibit movement of the set screw outwardly past the threaded block area and away from the opening of the bore to thereby inhibit removal of the set screw from the bore, the third length being shorter than the second length so that an entirety of the threaded block area can be disposed within the unthreaded set screw area between the threaded set screw area and the abutment, such that, with the threaded block area disposed within the unthreaded set screw area:

if turned in a first direction with respect to the block, the set screw is freely rotatable within the bore, but retained within the bore as the abutment of the set screw abuts the one or more block threads; and if turned in a second direction, opposite the first direction, with respect to the block, the one or more set screw threads are threadably engageable with the one or more block threads to move the set screw in an inward direction toward the opening of the bore.

14. The set screw apparatus of claim 13, wherein the set screw body includes a cylindrical shape.

15. The set screw apparatus of claim 13, wherein the set screw body is substantially tubular.

16. The set screw apparatus of claim 13, wherein the abutment is substantially annular.

17. The set screw apparatus of claim 13, wherein the block includes a passage fluidly coupled with the opening of the bore, the passage configured to selectively accept a proximal end of a therapy delivery element, wherein, with the proximal end of the therapy delivery element disposed within the passage, rotation of the set screw in the second direction with respect to the block causes the set screw to move in the inward direction with respect to the block to bear against the proximal end of the therapy delivery element.

18. The set screw apparatus of claim 17, wherein the passage is oriented within the block substantially perpendicularly to the bore.

* * * * *

UNITED STATES PATENT AND TRADEMARK OFFICE
CERTIFICATE OF CORRECTION

PATENT NO. : 9,068,587 B2  
APPLICATION NO. : 14/032316  
DATED : June 30, 2015  
INVENTOR(S) : Shahn S. Sage et al.

Page 1 of 1

It is certified that error appears in the above-identified patent and that said Letters Patent is hereby corrected as shown below:

On the title page, item 73, Assignee delete "Greatbach" and insert --Greatbatch--

Signed and Sealed this
Twenty-ninth Day of December, 2015

Michelle K. Lee
*Director of the United States Patent and Trademark Office*